United States Patent
Tomiyama et al.

(10) Patent No.: US 10,799,666 B2
(45) Date of Patent: Oct. 13, 2020

(54) STRESS ALLEVIATION SYSTEM AND STRESS ALLEVIATION METHOD

(71) Applicant: Panasonic Intellectual Property Management Co., Ltd., Osaka (JP)

(72) Inventors: Naomi Tomiyama, Kyoto (JP); Yasuko Iketsuki, Tokyo (JP); Atsushi Saso, Kanagawa (JP); Takamichi Matsusako, Tokyo (JP); Yuichi Aoki, Osaka (JP); Motoji Ohmori, Osaka (JP); Akira Asai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 254 days.

(21) Appl. No.: 15/803,786

(22) Filed: Nov. 5, 2017

(65) Prior Publication Data

US 2018/0140798 A1   May 24, 2018

(30) Foreign Application Priority Data

Nov. 22, 2016 (JP) ................. 2016-226681

(51) Int. Cl.
*A61M 21/02* (2006.01)
*A61B 5/0205* (2006.01)
(Continued)

(52) U.S. Cl.
CPC ......... *A61M 21/02* (2013.01); *A61B 5/02055* (2013.01); *A61B 5/165* (2013.01);
(Continued)

(58) Field of Classification Search
CPC .............................................. A61M 21/00–02
See application file for complete search history.

(56) References Cited

U.S. PATENT DOCUMENTS

| | | | |
|---|---|---|---|
| 2015/0061825 A1 | 3/2015 | Suzuki et al. | |
| 2016/0170998 A1* | 6/2016 | Frank ................ | G06F 16/24578 707/748 |

(Continued)

FOREIGN PATENT DOCUMENTS

| | | |
|---|---|---|
| JP | 6-000209 | 1/1994 |
| JP | 2004-284449 | 10/2004 |

(Continued)

*Primary Examiner* — Thaddeus B Cox
(74) *Attorney, Agent, or Firm* — Greenblum & Bernstein, P.L.C.

(57) ABSTRACT

A stress alleviation system, includes: a biological sensor measuring first biological data of a customer boarding transportation; an action application apparatus provided to a transportation seat and applying an action to the customer for alleviating a stressed state of the customer sitting on the seat; a stress data saver previously saving specific stress data where a customer identifier identifying the customer and a second stress indicator calculated using second biological data measured in past boarding of the customer are associated; a stressed state assessor assessing whether the customer is in the stressed state by calculating a first stress indicator of the customer on board using the first biological data of the customer, and by comparing the first stress indicator with the second stress indicator; and an action controller transmitting a control signal causing the action to the action application apparatus when the customer is assessed as in the stressed state.

17 Claims, 14 Drawing Sheets

(51) Int. Cl.
*A61B 5/00* (2006.01)
*B64D 11/06* (2006.01)
*B60N 2/90* (2018.01)
*A61B 5/16* (2006.01)
*A61H 23/02* (2006.01)
*B60N 2/02* (2006.01)
*A61M 21/00* (2006.01)
*A61B 5/024* (2006.01)
*A61B 5/053* (2006.01)
*A61B 5/08* (2006.01)
*B60N 2/20* (2006.01)

(52) U.S. Cl.
CPC ............ *A61B 5/486* (2013.01); *A61B 5/6891* (2013.01); *A61B 5/7278* (2013.01); *A61H 23/02* (2013.01); *B60N 2/0244* (2013.01); *B60N 2/976* (2018.02); *B64D 11/064* (2014.12); *A61B 5/0077* (2013.01); *A61B 5/024* (2013.01); *A61B 5/0533* (2013.01); *A61B 5/08* (2013.01); *A61B 2503/12* (2013.01); *A61H 2201/1645* (2013.01); *A61H 2201/5025* (2013.01); *A61H 2201/5058* (2013.01); *A61H 2230/04* (2013.01); *A61H 2230/105* (2013.01); *A61H 2230/305* (2013.01); *A61H 2230/425* (2013.01); *A61H 2230/505* (2013.01); *A61H 2230/655* (2013.01); *A61M 2021/0005* (2013.01); *A61M 2021/005* (2013.01); *A61M 2021/0022* (2013.01); *A61M 2021/0027* (2013.01); *A61M 2205/50* (2013.01); *A61M 2230/06* (2013.01); *A61M 2230/42* (2013.01); *A61M 2230/63* (2013.01); *B60N 2/20* (2013.01); *B60N 2002/0268* (2013.01)

(56) References Cited

U.S. PATENT DOCUMENTS

2016/0318395 A1* 11/2016 Cofer .................. B60K 28/066
2016/0354027 A1* 12/2016 Benson ................ A61M 21/02
2017/0069194 A1* 3/2017 Sharma .............. G08B 21/0461

FOREIGN PATENT DOCUMENTS

| JP | 2007-151933 | 6/2007 |
| JP | 2012-120206 | 6/2012 |
| JP | 2012-249797 | 12/2012 |
| JP | 2015-046065 | 3/2015 |
| JP | 2016-101307 | 6/2016 |
| WO | 2001/093746 | 12/2001 |

* cited by examiner

| SEAT IDENTIFIER | CUSTOMER IDENTIFIER | SPECIFIC STRESS INDICATOR |
|---|---|---|
| 3A | 10251451 | 108 |
| 10C | 87431 | 56 |

| CUSTOMER IDENTIFIER | BOARDING FLIGHT IDENTIFIER | STRESS INDICATOR (TIME-SERIES DATA) |
|---|---|---|
| 10251451 | AUGUST 15 PAL254 ITAMI → HANEDA | 115,··· |
|  | AUGUST 16 PAL265 HANEDA → ITAMI | 89,··· |
|  | AUGUST 23 PAL1378 ITAMI → SENDAI | 119,··· |
| 2713819 | SEPTEMBER 1 PAL221 HANEDA → NAHA | 56,··· |

| CUSTOMER IDENTIFIER | SPECIFIC STRESS INDICATOR |
|---|---|
| 10251451 | 108 |
| 2713819 | 56 |

| BOARDING FLIGHT IDENTIFIER | SEAT IDENTIFIER | CUSTOMER IDENTIFIER |
|---|---|---|
| AUGUST 15 PAL254 ITAMI → HANEDA | LINE 3 A | 10251451 |
| ... | ... | ... |

| CUSTOMER IDENTIFIER | NAME | FREQUENT FLYER POINTS | ATTRIBUTE |
|---|---|---|---|
| U03 | XXX | 3000 | PREMIUM |
| U04 | YYY | 200 | |
| ... | ... | ... | ... |

STRESS ALLEVIATION SYSTEM AND STRESS ALLEVIATION METHOD

BACKGROUND

1. Technical Field

The present disclosure relates to a technique for alleviating stress to a customer in transportation such as an airplane.

2. Description of the Related Art

In recent years, various techniques which use vital data of a person to estimate stress to the person have been suggested. Accordingly, studies of techniques for providing various services for users by using the technique have been progressing. Japanese Unexamined Patent Application Publication No. 2016-101307 discloses that in a case where a target person with high stress is present, such a situation is notified to a flight attendant or the like, and the flight attendant or the like preferentially takes care of the target person or provides service with full attention for the target person.

SUMMARY

One non-limiting and exemplary embodiment provides a technique for alleviating stress to a customer on board transportation such as an airplane by using biological data.

In one general aspect, the techniques disclosed here feature a stress alleviation system, including: a biological sensor that measures first biological data of a customer on board a transportation; an action application apparatus that is provided to a seat of the transportation and applies an action to the customer for alleviating a stressed state of the customer sitting on the seat; a stress data saver that in advance saves specific stress data in which a customer identifier and a second stress indicator are associated with each other, the customer identifier identifying the customer, the second stress indicator being calculated by using second biological data of the customer, the second biological data being measured while on board in the past; a stressed state assessor that assesses whether or not the customer is in the stressed state by calculating a first stress indicator of the customer on board using the first biological data of the customer, and by comparing the first stress indicator with the second stress indicator; and an action controller that transmits a control signal to the action application apparatus provided to the seat of the customer in a case where the customer is assessed as in the stressed state, the control signal causing the action application apparatus to apply the action to the customer.

It should be noted that general or specific embodiments may be implemented as an element, a device, an apparatus, a system, an integrated circuit, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a diagram that illustrates one example of a data configuration of a specific stress table that is stored in a stress data saving unit;

FIG. 5 is a diagram that illustrates one example of a data configuration of a stress history table that stores one or more pieces of stress history data;

FIG. 6 is a diagram that illustrates one example of a data configuration of a specific stress table;

FIG. 7 is a diagram that illustrates one example of a data configuration of a reservation information table;

FIG. 15 is a diagram that illustrates one example of a data configuration of a customer table that is used in a stress alleviation system according to a fourth embodiment of the present disclosure.

Figure 1:
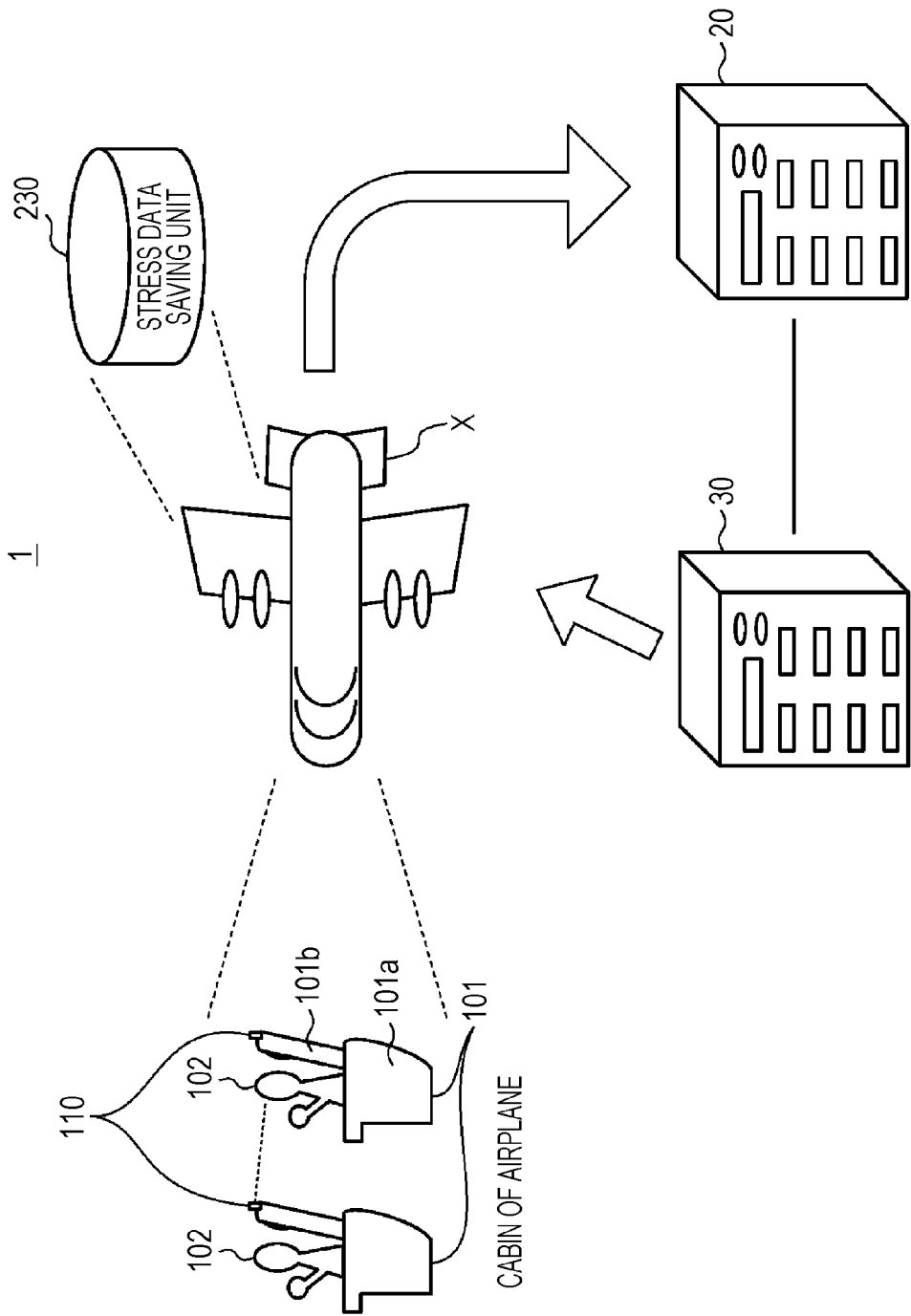
FIG. 1 is a diagram that illustrates one example of a general configuration of a stress alleviation system according to a first embodiment of the present disclosure.

DETAILED DESCRIPTION (Underlying Knowledge Forming Basis of the Present Disclosure)

Above Japanese Unexamined Patent Application Publication No. 2016-101307 discloses a technique of detecting biological information of a target person who sits on a seat by a pressure sensing tube provided to the seat of an airplane; assessing stress of the target person from the detected biological information, and performing a notification to a flight attendant; a pilot, or the like in a case where the assessed stress is high.

However, a fundamental purpose of Japanese Unexamined Patent Application Publication No. 2016-101307 is to provide a biological information acquisition apparatus that may improve detection accuracy of the biological information of the target person (paragraph [0008]). Japanese Unexamined Patent Application Publication No. 2016-101307 only discloses a specific example in which the biological information acquisition apparatus is arranged in a seat portion of an airplane, as one aspect. Further, Japanese Unexamined Patent Application Publication No. 2016-

101307 only discloses that a flight attendant or a pilot provides a service with full attention for a target person with high stress, as an effect of the specific example.

In such a manner, in Japanese Unexamined Patent Application Publication No. 2016-101307, alleviation of stress to a target person is dealt with by service by a flight attendant. Consequently, in a case where a basic cause of the stress is included in the service itself by the flight attendant, the stress to the target person may not be alleviated.

Further, in Japanese Unexamined Patent Application Publication No. 2016-101307, for example, in a case where the change rate of the stress value that is calculated from pressure sensing data in a predetermined period is a predetermined value or higher, the target person is assessed as in a stressed state. However, whether or not the target person is in the stressed state is not assessed while taking into consideration past stress values of the target person. Thus, in Japanese Unexamined Patent Application Publication No. 2016-101307, whether or not the target person is in the stressed state may not be assessed with a determination reference that is suitable for the target person.

It is desirable to provide a technique for alleviating stress to a customer who is boarded on an airplane by using biological data.

A stress alleviation system, comprising:

a biological sensor that measures first biological data of a customer on board a transportation;

an action application apparatus that is provided to a seat of the transportation and applies an action to the customer for alleviating a stressed state of the customer sitting on the seat;

a stress data saver that in advance saves specific stress data in which a customer identifier and a second stress indicator are associated with each other, the customer identifier identifying the customer, the second stress indicator being calculated by using second biological data of the customer, the second biological data being measured while on board in the past;

a stressed state assessor that assesses whether or not the customer is in the stressed state by calculating a first stress indicator of the customer on board using the first biological data of the customer, and by comparing the first stress indicator with the second stress indicator; and an action controller that transmits a control signal to the action application apparatus provided to the seat of the customer in a case where the customer is assessed as in the stressed state, the control signal causing the action application apparatus to apply the action to the customer.

In this aspect, a stress indicator of each of the customers who is boarded is calculated by using the biological data, which is measured by the biological sensor, of each of the customers on board an airplane. Then, each of the calculated stress indicators is compared with a specific stress indicator that is calculated from the biological data measured in the past, and whether or not each of the customers on board is the stressed customer who is in a stressed state is thereby assessed.

Then, the control signal which causes the action for alleviating the stress to each of the stressed customer is transmitted to the action application apparatuses provided to the respective seats on which the respective stressed customers sit.

In such a manner, in this aspect, the stressed states of the respective stressed customers are alleviated by the actions that are applied to the customers by the action application apparatuses provided to the respective seats on which the respective stressed customers sit. Consequently, even in a case where a cause of the stress to each of the stressed customers is included in the service by the flight attendant, the stress to each of the stressed customers may be alleviated.

Further, whether or not each of the customers is the stressed customer is assessed in accordance with the specific stress indicator that is calculated from the biological data measured in the past as a reference. Consequently, whether or not each of the customers is the stressed customer may be assessed in accordance with a determination reference that corresponds to each of the customers, and whether or not each of the customers is in the stressed state may thus be assessed accurately.

Further, in the above aspect, the action application apparatus may include a reclining mechanism that inclines the seat, and the action controller may transmit the control signal that causes the reclining mechanism to adjust an inclination amount of the seat of the customer.

In this aspect, because the inclination amount of the seat of each of the stressed customers is adjusted, each of the stressed customers is relaxed, and the stress to each of the stressed customers may thereby be alleviated.

In the above aspect, the action application apparatus may include a massage mechanism that massages the customer sitting on the seat, and the action controller may transmit the control signal that causes the massage mechanism provided to the seat of the customer to turn on.

In this aspect, because the massage mechanism provided to the seat of each of the stressed customers is turned on, each of the stressed customers is relaxed, and the stress to each of the stressed customers may thereby be alleviated.

In the above aspect, the action application apparatus may include a content output apparatus that outputs a content for alleviating the stressed state of the customer sitting on the seat, and the action controller may transmit the control signal that causes the content output apparatus corresponding to the seat of the customer to output the content.

In this aspect, because the content for removing the stress is output for each of the stressed customers, each of the stressed customers is caused to concentrate on the content, and the stress to each of the stressed customers may thereby be alleviated.

In the above aspect, the stressed state assessor may assess the customer as in the stressed state in a case where a difference between the second stress indicator and the first stress indicator is greater than a predetermined threshold value.

In this aspect, because the customer is assessed as the stressed customer in a case where the difference between the stress indicator and the specific stress indicator is greater than the threshold value, whether or not the customer is the stressed customer may be assessed in accordance with a determination reference that corresponds to each of the customers.

In the above aspect, the action controller may change a type or strength of the action, in a case where the customer is assessed as in the stressed state even after the action is applied to the customer.

In this aspect, in a case where the stressed customer maintains the stressed state even in a case where a certain action is applied to the stressed customer, another kind of action is applied to the stressed customer, and the possibility of making the stressed customer not in the stressed state may thus be made higher.

In the above aspect, the action controller may apply the action with which the first stress indicator becomes a minimum among the actions applied to the customer, in a case where the stressed state of the customer is not removed even when the type or strength of the action are changed.

In this aspect, in a case where the stressed customer maintains the stressed state even in a case where a type of actions are changed, the action with which the stress indicator is the minimum is applied to the stressed customer, and the stress to the stressed customer may thus be alleviated as much as possible.

In the above aspect, the stressed state assessor may
  assess the customer as in the stressed state in a case where the customer is a customer who satisfies a predetermined condition and where a difference between the first stress indicator and the second stress indicator is greater than a first threshold value, and
  assess the customer as in the stressed state in a case where the customer is a customer who does not satisfy the predetermined condition and where the difference is greater than a second threshold value that is greater than the first threshold value.

In this aspect, the stress to the second customer who is more important than the first customer may be alleviated early.

First Embodiment

FIG. 1 is a diagram that illustrates one example of a general configuration of a stress alleviation system 1 according to a first embodiment of the present disclosure. The stress alleviation system 1 includes one or more biological sensors 110 that are mounted on one or more seats 101 of an airplane X, a stress data saving unit 230 that saves a specific stress indicator of each customer 102 who boards the airplane X, a stress management apparatus 20 that manages the stress indicator of each of the customers 102 that is obtained from biological data measured by the biological sensor 110, and a reservation management apparatus 30 that manages reservation data for the airplane X of each of the customers 102.

The airplane X is a passenger plane that is owned by an airline company, for example. The airplane X includes one or more seats 101 on which the customers 102 sit. The biological sensors 110 are respectively provided to one or more seats 101. However, this is one example, and in a case where the biological sensor 110 is configured with a biological sensor that is capable of simultaneously measuring biological data of plural persons, one biological sensor 110 may be provided for plural seats that correspond to plural persons whose biological data are measurable.

The seat 101 includes a seat portion 101a that supports a lower back of the customer 102 and a back portion 101b that supports a back of the customer 102. The biological sensor 110 is configured with a millimeter-wave radar, for example, and is arranged to be opposed to the customer 102 who sits on the rear seat 101 in the back portion 101b. In the example of FIG. 1, the biological sensor 110 is arranged at an upper end of the back portion 101b. However, this is one example, and the biological sensor 110 may be arranged at the back portion 101b to be positioned in front of a face of the customer 102. The directivity of the biological sensor 110 is set such that a millimeter wave (measurement wave) radiated to the customer 102 is radiated to the vicinity of the face of the sitting customer 102.

Further, in the example of FIG. 1, the biological sensor 110 is provided to the back portion 101b. However, this is one example, and the biological sensor 110 may be provided to a ceiling in a cabin of the airplane X. In this case, the biological sensor 110 may be provided to a ceiling to be positioned directly above each of the seats 101.

The stress data saving unit 230 is configured with a non-volatile storage apparatus that is provided in the airplane X. The stress management apparatus 20 is configured with a computer that includes a CPU, a ROM, a RAM, a communication apparatus, and so forth, for example, and is connected with the airplane X via a predetermined network so as to be capable of communication. The reservation management apparatus 30 is configured with a computer that includes a CPU, a ROM, a RAM, a communication apparatus, and so forth, for example, and is connected with the stress management apparatus 20 and the airplane X via a predetermined network so as to be capable of communication.

Figure 2:
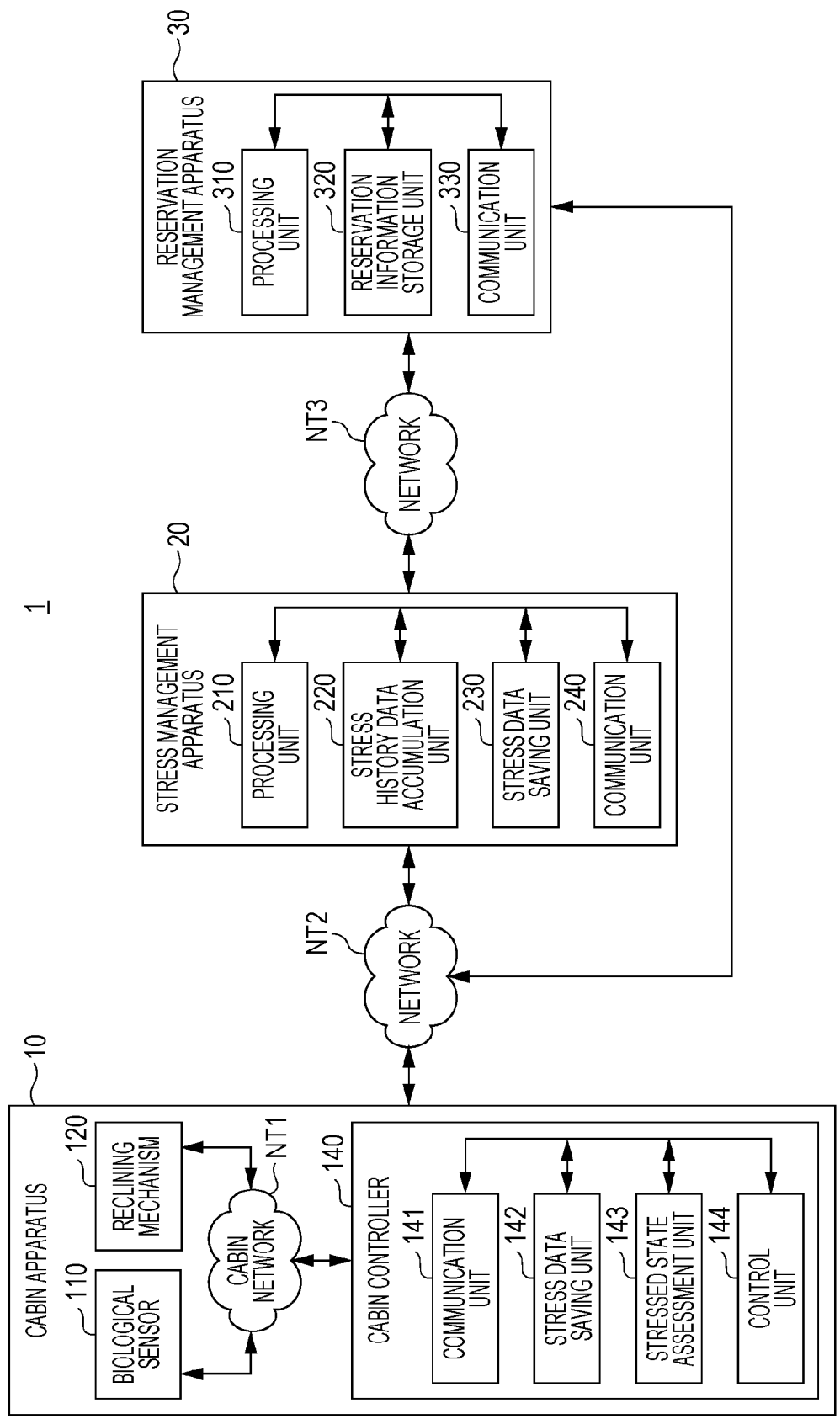
FIG. 2 is a block diagram that illustrates a configuration of the stress alleviation system according to the first embodiment of the present disclosure.

FIG. 2 is a block diagram that illustrates a configuration of the stress alleviation system 1 according to the first embodiment of the present disclosure. The stress alleviation system 1 includes a cabin apparatus 10 that is provided to the airplane X and the stress management apparatus 20 and the reservation management apparatus 30 which are illustrated in FIG. 1. The cabin apparatus 10 and the stress management apparatus 20 are connected via a network NT2 so as to be capable of mutual communication. As the network NT2, a public telecommunication network may be employed which includes a radio communication network such as Wi-Fi® which is capable of communication between an airplane and a base station on the ground.

The stress management apparatus 20 and the reservation management apparatus 30 are connected via a network NT3 so as to be capable of mutual communication. As the network NT3, a public telecommunication network may be employed which includes a cellular phone communication network, a Wi-Fi® communication network, and an Internet communication network, and so forth. The reservation management apparatus 30 is connected with the cabin apparatus 10 via the network NT2. Note that for convenience of description, FIG. 2 separately illustrates the network NT2 and the network NT3. However, this is one example, and both of the networks may be the same.

The cabin apparatus 10 is configured with a computer that is provided in the airplane X, for example, and includes the biological sensor 110 (one example of a biological sensor), a reclining mechanism 120, a cabin controller 140, and a cabin network NT1.

The biological sensor 110 is connected with the cabin controller 140 via the cabin network NT1 so as to be capable of communication, measures the biological data of the customer 102 who sits on the seat 101, and transmits the measured biological data to the cabin controller 140 via the cabin network NT1. In recent years, a measurement technique has been known which simultaneously and contactlessly measures the biological data of plural persons by using a millimeter-wave radar. Specifically, this measurement technique radiates a millimeter wave of 60 GHz band to a person, for example, extracts a heartbeat signal from a measured radar signal, extracts phase characteristic points from the extracted heartbeat signal, and estimates heartbeat intervals from a time-series pattern of the extracted phase characteristic points.

Then, in a case where the heartbeat intervals may be estimated, a frequency analysis of the fluctuation of the heartbeat intervals is performed as disclosed in Japanese Patent No. 5257525, for example, and the stress to a person may thereby be detected. Accordingly, in this embodiment, the millimeter-wave radar is employed as the biological sensor 110.

Further, Japanese Unexamined Patent Application Publication No. 2016-101307, which is described in description of the related art, discloses a technique for measuring the biological data of a target person based on a pressure sensing tube attached to the seat portion 101a and the signal that corresponds to an internal pressure which occurs in the pressure sensing tube. Accordingly, in the present disclosure, the biological information of the customer 102 may be measured by using the technique disclosed in Japanese Unexamined Patent Application Publication No. 2016-101307.

The reclining mechanism 120 is provided to each of one or more seats 101 and inclines the back portion 101b of the seat 101 rearward or forward in accordance with a control signal that is transmitted from the cabin controller 140. In this embodiment, each of the seats 101 is a reclining seat that is configured such that the back portion 101b is capable of inclining forward and rearward about an attachment base of the seat portion 101a as the origin. The reclining mechanism 120 is includes a motor, a transmission mechanism that transmits rotational force of the motor to the back portion 101b, a communication unit that receives a control signal, and so forth. The reclining mechanism 120 causes the back portion 101b to incline rearward or forward by the rearward or forward inclination amount that is indicated by the control signal. Here, forward represents the traveling direction of the airplane X, and rearward represents the opposite direction to the traveling direction. The cabin network NT1 is correspondent to a wireless LAN or a wired LAN, for example.

The cabin controller 140 is configured with a computer with a communication function that has a CPU, a ROM, and a RAM and conducts general control of the cabin apparatus 10. The cabin controller 140 includes a communication unit 141, a stress data saving unit 142, a stressed state assessment unit 143, and a control unit 144 (one example of an action control unit).

The communication unit 141 is configured with a communication apparatus for connecting the cabin controller 140 with the cabin network NT1 and a communication apparatus for connecting the cabin apparatus 10 with the network NT2.

The stress data saving unit 142 in advance saves specific stress data in which a customer identifier of each of the customers 102 who on board sits on each of the seats 101 of the airplane X are associated with the specific stress indicator which indicates the stress to each of the customers 102 which is calculated by using the biological data measured by the biological sensor 110 in the past.

FIG. 3 is a diagram that illustrates one example of a data configuration of a specific stress table T1 that is saved in the stress data saving unit 142. The specific stress table T1 is a database in which one piece of specific stress data is assigned to one record and includes fields of "seat identifier", "customer identifier", and "specific stress indicator". "Seat identifier" is an identifier for identifying the seat on which each of the customers 102 sits.

Figure 4:
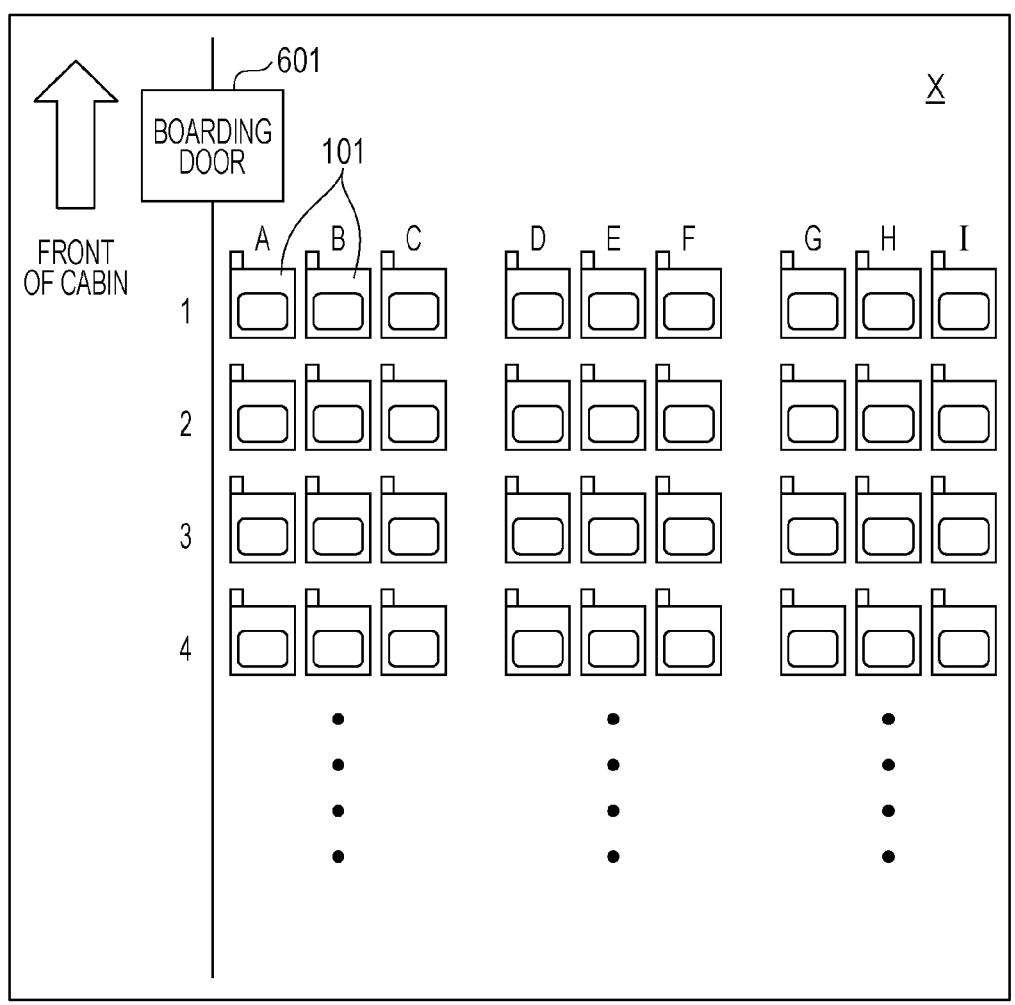
FIG. 4 is a diagram that illustrates one example of a seat arrangement diagram which illustrates arrangement of seats in a cabin of an airplane.

FIG. 4 is a diagram that illustrates one example of a seat arrangement diagram which illustrates arrangement of the seats 101 in the cabin of the airplane X. The arrow in this seat arrangement diagram points towards the front of the cabin. Further, in this seat arrangement diagram, the seat identifier is given to each of the seats 101 by a pair of a value that indicates the order in a line in the transverse direction and a symbol that indicates the order in a line in the longitudinal direction. Values such as "1", "2", and "3" are assigned to the lines in the transverse direction in the order from the front, and symbols such as "A", "B", and "C" are assigned to the lines in the longitudinal direction from the left to the right. In this example, because nine lines of seats 101 in the longitudinal direction are provided, nine symbols of "A" to "I" are assigned to the lines in the longitudinal direction. Accordingly, the seat 101 that is positioned in the upper left apex has the seat identifier "1A", and the seat 101 that is in the next position on the right has the seat identifier "1 B". Note that in FIG. 4, in all the lines in the transverse direction, the nine lines of seats 101 in the longitudinal direction are provided. However, this is one example, and 10 or more or 8 or less lines of seats 101 may be provided. A boarding door 601 that communicates with the outside of the airplane X is provided in front of the seat of the seat identifier "1A".

FIG. 3 will be referred to. "Customer identifier" is an identifier for identifying each of the customers 102 who boards the airplane X. As "customer identifier", for example, an identifier which uniquely distinguishes each of the customers 102 to be a management target (a customer who uses or has used the airline company which owns the airplane X) is employed. In the field of "specific stress indicator", the specific stress indicator is stored. The specific stress indicator is the average value of the stress indicators which are calculated from the biological data. The biological data have been measured by the biological sensors 110 in the airplanes X which each of the customers 102 has boarded in the past.

In the example of FIG. 3, only two records in which the specific stress data of two customers 102 are registered are illustrated. However, actually, the specific stress data of each of the customers 102 who boards the airplane X are registered.

FIG. 2 will be referred to again. The stressed state assessment unit 143 calculates the stress indicator of each of the customers 102 who is boarded by using the biological data, which is measured by the biological sensor 110, of each of the customers 102 who is boarded on the airplane X. Then, the stressed state assessment unit 143 compares the calculated stress indicator of each of the customers 102 with the specific stress indicator of each of the customers 102 and thereby assesses whether or not each of the customers 102 who is boarded is a stressed customer who is in a stressed state.

Here, the stressed state assessment unit 143 may execute an assessment process about whether the customer 102 is the stressed customer in a predetermined assessment period, for example. Here, in the assessment period, the stressed state assessment unit 143 estimates the heartbeat intervals by using the above-described scheme from time-series data of the biological data measured by the biological sensor 110 at predetermined sampling intervals. Then, the stressed state assessment unit 143 performs the frequency analysis of the estimated heartbeat intervals, thereby detects a level HF of a high-frequency peak that occurs around a frequency of 0.3 Hz and a level LF of a low-frequency peak that occurs around 0.1 Hz, and may thereby calculate LF/HF as the stress indicator. Note that because the value of LF/HF increases as the stress becomes higher, the higher value of the stress indicator indicates the higher stress.

Further, the stressed state assessment unit 143 calculates the difference by subtracting the specific stress indicator of each of the customers 102 from the calculated stress indicator of each of the customers 102 and may thereby assess the customers 102 for whom the calculated difference is greater than a predetermined threshold value as the stressed customer. Here, because the specific stress indicator is the average value of the stress indicators at times when the customer 102 boarded the airplanes X in the past, the specific stress indicator may be considered as the stress indicator of the customer 102 in a usual condition. Thus, the greater calculated difference indicates the higher stress to the customer 102. Further, it is possible to assess whether or not the customer 102 is the stressed customer from the absolute value of the calculated stress indicator. However, the stress indicator in the usual condition is different depending on the customer 102. Thus, in this embodiment, whether or not the customer 102 is the stressed customer is assessed by using the above difference. Accordingly, it is possible to assess whether or not the customer 102 is the stressed customer while taking into consideration the stress indicator in the usual condition that differs depending on each of the customers 102.

Referring to FIG. 3, with respect to the customer 102 of the customer identifier "10251451", in a case where the calculated stress indicator is "120", for example, because the specific stress indicator of this customer 102 is "108", 120−108=12 is the difference for this customer 102. Then, in a case where the difference "12" is greater than the threshold value, this customer 102 is assessed as the stressed customer. The stressed state assessment unit 143 executes this process for each of the customers 102 who is boarded on the airplane X and thereby assesses whether or not the customer 102 is the stressed customer. Note that, as the threshold value, an empirically obtained value may be employed at which the customer 102 is assumed to be in an excited state and to have stress in a case where the difference becomes the threshold value or greater.

FIG. 2 will be referred to again. The control unit 144 transmits a control signal to the reclining mechanism 120 of the seat 101 on which the customer 102 sits who is assessed as the stressed customer by the stressed state assessment unit 143 via the cabin network NT, and the control unit 144 adjusts the inclination amount of the back portion 101b such that the inclination amount of the back portion 101b becomes an appropriate inclination amount for the stressed customer. Accordingly, the stress to the stressed customer may be reduced.

Further, the control unit 144 receives the specific stress data of each of the customers 102 who boards the airplane X, which are transmitted from the reservation management apparatus 30 immediately before the airplane X takes off, via the network NT2, and the control unit 144 registers the specific stress data in the specific stress table T1.

Further, for example, when the airplane X arrives at a destination, the control unit 144 associates the time-series data of the stress indicator that is calculated by the stressed state assessment unit 143 in each of the assessment periods with the customer identifier and a boarding flight identifier and transmits the time-series data as stress history data to the stress management apparatus 20 by using the communication unit 141. Accordingly, the stress history data are registered in a stress history table T2 (FIG. 5), which will be described later.

Note that the control unit 144 may associate the calculated stress indicator with the customer identifier and the boarding flight identifier at each time when the stressed state assessment unit 143 calculates the stress indicator and transmit the calculated stress indicator to the stress management apparatus 20 by using the communication unit 141.

The stress management apparatus 20 includes a processing unit 210, a stress history data accumulation unit 220, the stress data saving unit 230, and a communication unit 240. The processing unit 210 conducts general control of the stress management apparatus 20. The stress history data accumulation unit 220 accumulates the stress history data under control of the processing unit 210. FIG. 5 is a diagram that illustrates one example of a data configuration of the stress history table T2 that stores one or more pieces of stress history data. The stress history data are data that indicate the stress indicator for each of the boarding flights of the airplanes X with respect to each of the customers 102. The stress history table T2 is a database in which one piece of stress history data is assigned to one record and includes fields of "customer identifier", "boarding flight identifier", and "stress indicator", "Customer identifier" is the same as FIG. 3. "Boarding flight identifier" is data that identify the airplane X which each of the customers 102 boards and is configured with "date" data, "flight number" data, and "flight route" data. "Date" data indicate the operation date of the concerned boarding flight. "Flight number" data indicate the name of the concerned boarding flight, "Flight route" data indicate the departure place and the destination place of the concerned boarding flight. For example, in "boarding flight identifier" in the record in the first row of FIG. 5, "August 15" matches the "date" data, "PAL254" matches the "flight number" data, and "Itami→Haneda" matches the "flight route" data. Note that the "date" data are configured with "month+day" but may be configured with "month+day+year".

In the field of "stress indicator", the stress indicator of the customer 102 in the concerned boarding flight is registered. Here, in the field of "stress indicator", for example, the time-series data of the stress indicator that is calculated by the stressed state assessment unit 143 in each of the assessment periods in the concerned boarding flight are registered.

For example, because the customer 102 of the customer identifier "10251451" has boarded three boarding flights, the stress history table T2 includes three records in which three pieces of stress history data of this customer 102 are registered.

Here, the cabin controller 140 transmits the above-described stress history data to the stress management apparatus 20 when the boarding flight arrives at the destination. The processing unit 210 of the stress management apparatus 20 receives the stress history data by using the communication unit 240, thereby registers the stress history data in the stress history table, and may thereby generate the stress history table T2. Note that the calculated stress indicator, which is associated with the customer identifier and the boarding flight identifier, may be transmitted to the stress management apparatus 20 at each time when the cabin controller 140 calculates the stress indicator. In this case, the processing unit 210 may register the stress indicator in the field of "stress indicator" of the concerned record at each time when the stress indicator is received, in a time-series manner.

The stress data saving unit 230 saves a specific stress table T3 (FIG. 6) in which plural pieces of specific stress data are registered. FIG. 6 is a diagram that illustrates one example of a data configuration of the specific stress table T3. The specific stress table T3 is a database in which the specific stress indicator of one customer is registered to one record and includes fields of "customer identifier" and "specific stress indicator".

"Customer identifier" and "specific stress indicator" are the same as FIG. 3. Note that the specific stress table T3 is not provided with the field of "seat identifier" that is indicated in the specific stress table T1 of FIG. 3. This is because "seat identifier" is given by the reservation management apparatus 30 but is not given by the stress management apparatus 20. Further, because the specific stress table T1 is transmitted to the boarding flight (airplane X), the specific stress table T1 stores the specific stress data of each of the customers 102 who boards the boarding flight. However, the specific stress data of all the customers 102 to be management targets are registered in the specific stress table T3.

FIG. 2 will be referred to. The communication unit 240 is configured with a communication apparatus for connecting the stress management apparatus 20 with the network NT2 and the network NT3. In this embodiment, the communication unit 240 receives the stress history data transmitted from the cabin controller 140 via the network NT2. Further, the communication unit 240 transmits the specific stress data stored in the stress data saving unit 230 to the reservation management apparatus 30 via the network NT3.

The reservation management apparatus 30 includes a processing unit 310, a reservation information storage unit 320, and a communication unit 330. The processing unit 310 conducts general control of the reservation management apparatus 30. The reservation information storage unit 320 in advance stores a reservation information table T4 (FIG. 7). FIG. 7 is a diagram that illustrates one example of a data configuration of the reservation information table T4. The reservation information table T4 is a database in which one piece of reservation information is registered in one record and includes fields of "boarding flight identifier", "seat identifier", and "customer identifier". The reservation information is information that indicates which seat of which boarding flight is reserved with respect to each of the customers 102.

"Boarding flight identifier" and "customer identifier" are the same as FIG. 5, and "seat identifier" is the same as FIG. 3. In FIG. 7, the reservation information is registered which indicates that the customer 102 of the customer identifier "10251451" has reserved the seat of the seat identifier "line 3 A" for the boarding flight of the boarding flight identifier "August 15, PAL254, Itami→Haneda".

Note that in the example of FIG. 7, only one piece of reservation information is illustrated. However, actually, pieces of reservation information for all the seats of all the boarding flights to be management targets are registered.

In a case where the specific stress data transmitted from the stress management apparatus 20 are received by the communication unit 330, the processing unit 310 extracts "seat identifier" of the boarding flight which the customer 102 of "customer identifier" included in the received specific stress data then boards from the reservation information table T4. The processing unit 310 associates the extracted "seat identifier" with the received specific stress data and transmits the specific stress data to the cabin apparatus 10 by using the communication unit 330. Accordingly, as illustrated in FIG. 3, the cabin apparatus 10 may store the specific stress data in which "seat identifier" is associated with "customer identifier" and "specific stress indicator".

The communication unit 330 is configured with a communication apparatus for connecting the reservation management apparatus 30 with the network NT3.

Figure 8:
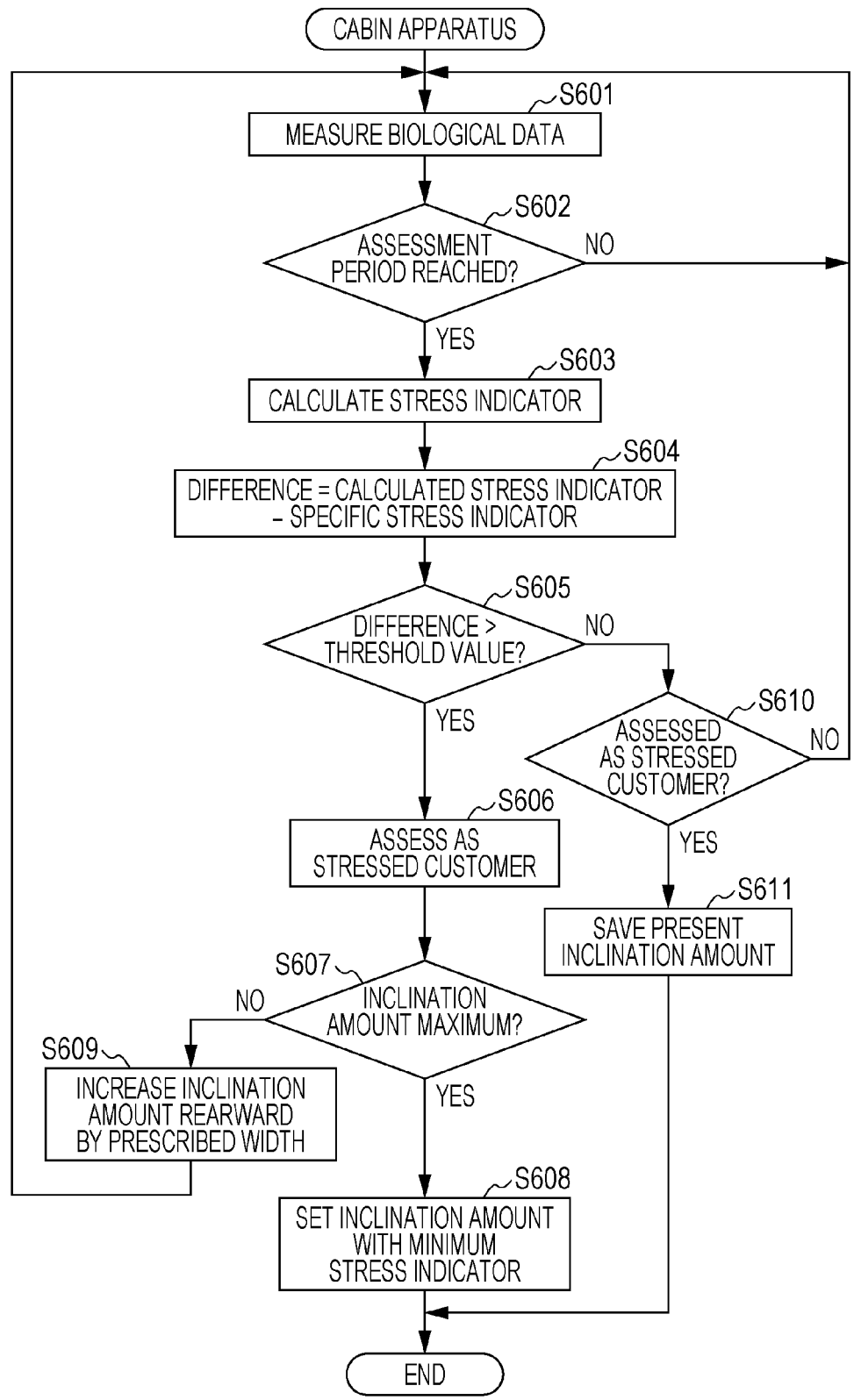
FIG. 8 is a flowchart that illustrates one example of a process of a cabin apparatus according to the first embodiment of the present disclosure.

FIG. 8 is a flowchart that illustrates one example of a process of the cabin apparatus 10 according to the first embodiment of the present disclosure. This flowchart is repeatedly executed in each of the above-described assessment periods, for example. Further, in this flowchart, a description will be made about the process for a certain customer 102 (hereinafter referred to as target customer) as an example. Further, in this flowchart, it is assumed that the minimum inclination amount in which the rearward inclination amount of the back portion 101b is the minimum is set as an initial inclination amount.

First, the biological sensor 110 that has the target customer as a measurement target measures the biological data at the predetermined sampling intervals (S601). Next, in a case where the assessment period is reached (YES in S602), the stressed state assessment unit 143 calculates the stress indicator of the target customer by using the time-series data of the biological data measured in the assessment period (S603). On the other hand, in a case where the assessment period is not reached (NO in S602), the process is returned to S601.

Next, the stressed state assessment unit 143 calculates the difference by subtracting the specific stress indicator of the target customer that is registered in the specific stress table T1 from the stress indicator of the target customer that is calculated in S603 (S604).

Next, the stressed state assessment unit 143 assesses whether or not the difference calculated in S604 is greater than the threshold value (S605). In a case where the difference calculated in S604 is greater than the threshold value (YES in S605), the stressed state assessment unit 143 assesses the target customer as the stressed customer (S606). On the other hand, in a case where the difference calculated in S604 is not greater than the threshold value (NO in S605), the process progresses to S610.

Next, in a case where the inclination amount does not become the maximum (NO in S607), the control unit 144 transmits the control signal for increasing the inclination amount rearward by a predetermined width to the reclining mechanism 120 of the target customer (S609) and returns the process to S601.

On the other hand, in a case where the inclination amount is the maximum (YES in S607), the inclination amount may not be adjusted any more. Thus, the control unit 144 transmits the control signal for setting the inclination amount at which the stress indicator is the minimum to the reclining mechanism 120 of the target customer (S608) and finishes the process. Accordingly, even in a case where the inclination amount at which the difference in S604 is the threshold value or less may not be searched for in the range between the minimum inclination amount and the maximum inclination amount, the seat 101 is set to the inclination amount at which the stress indicator is the minimum, and the stress to the target customer may thereby be alleviated as much as possible.

In S610, in a case where the target customer is already assessed as the stressed customer (YES in S610), the control unit 144 associates the present inclination amount with the customer identifier of the target customer and saves the present inclination amount as a learned inclination amount (S611). Accordingly, the inclination amount that does not make the target customer in the stressed state may be learned. In this case, the control unit 144 transmits the learned inclination amount to the stress management apparatus 20 by using the communication unit 141 and may thereby save the learned inclination amount. This learned inclination amount may be employed as the initial inclination amount of the back portion 101b in the next time when the target customer boards the airplane X, for example. Note that in a case where the reservation management apparatus 30 makes an acquisition request, which will be described later, for specific stress data, the stress management apparatus 20 may associate the learned inclination amount with the specific stress data as a transmission target and may thereby transmit the specific stress data to the reservation management apparatus 30.

On the other hand, in a case where the target customer is not assessed as the stressed customer (NO in S610), the control unit 144 returns the process to S601. Accordingly, monitoring about whether or not the target customer is the stressed customer is continued.

Figure 9:
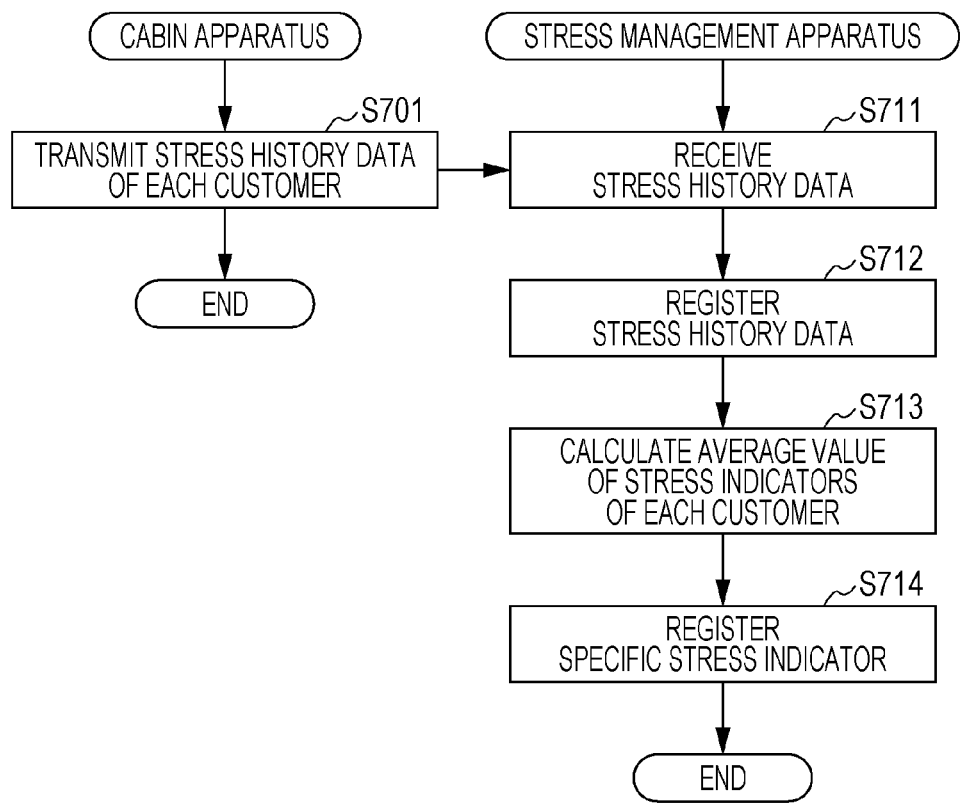
FIG. 9 is a flowchart that illustrates one example of a process in which stress history data are transmitted from the cabin apparatus to a stress management apparatus in the stress alleviation system according to the first embodiment of the present disclosure.

Next, a description will be made about a process in which the cabin apparatus 10 transmits the stress history data to the stress management apparatus 20. FIG. 9 is a flowchart that illustrates one example of the process in which the stress history data are transmitted from the cabin apparatus 10 to the stress management apparatus 20 in the stress alleviation system 1 according to the first embodiment of the present disclosure.

First, when the boarding flight arrives at the destination, the control unit 144 of the cabin apparatus 10 transmits the stress history data of each of the customers 102 who boards the boarding flight to the stress management apparatus 20 by using the communication unit 141 (S701). Here, as illustrated in FIG. 5, the stress history data are data in which the customer identifier, the boarding flight identifier, and the time-series data of the stress indicator are associated with each other.

Next, the communication unit 240 of the stress management apparatus 20 receives the stress history data of each of the customers 102 of the boarding flight (S711).

Next, the processing unit 210 of the stress management apparatus 20 registers the received stress history data in the stress history table T2 (S712). Accordingly, the stress history data are accumulated in the stress management apparatus 20.

Next, the processing unit 210 of the stress management apparatus 20 calculates the average value of the stress indicators of each of the customers 102 by using the time-series data of the stress indicator that are registered in the stress history table T2 (S713). In the example of FIG. 5, with respect to the customer 102 of the customer identifier "10251451", three pieces of stress history data are present, and the time-series data of the stress indicators of "115, . . . ", "89, . . . ", and "119, . . . " are respectively registered in the fields of "stress indicator". Thus, the average value of the stress indicators of this customer is the value that results from averaging all the values that are "115, . . . ", "89, . . . ", and "119, . . . ". The average values of the stress indicators are similarly calculated for the other customers 102.

Next, the processing unit 210 registers the average value of the stress indicators of each of the customers 102 as the specific stress indicator of each of the customers 102 in the specific stress table T3 (S714). In the example of FIG. 6, because the average value of the stress indicators of the customer 102 of the customer identifier "10251451" is calculated as "108", "108" is registered in the field of the specific stress indicator of this customer 102. The specific stress indicators are similarly registered for the other customers 102.

Figure 10:
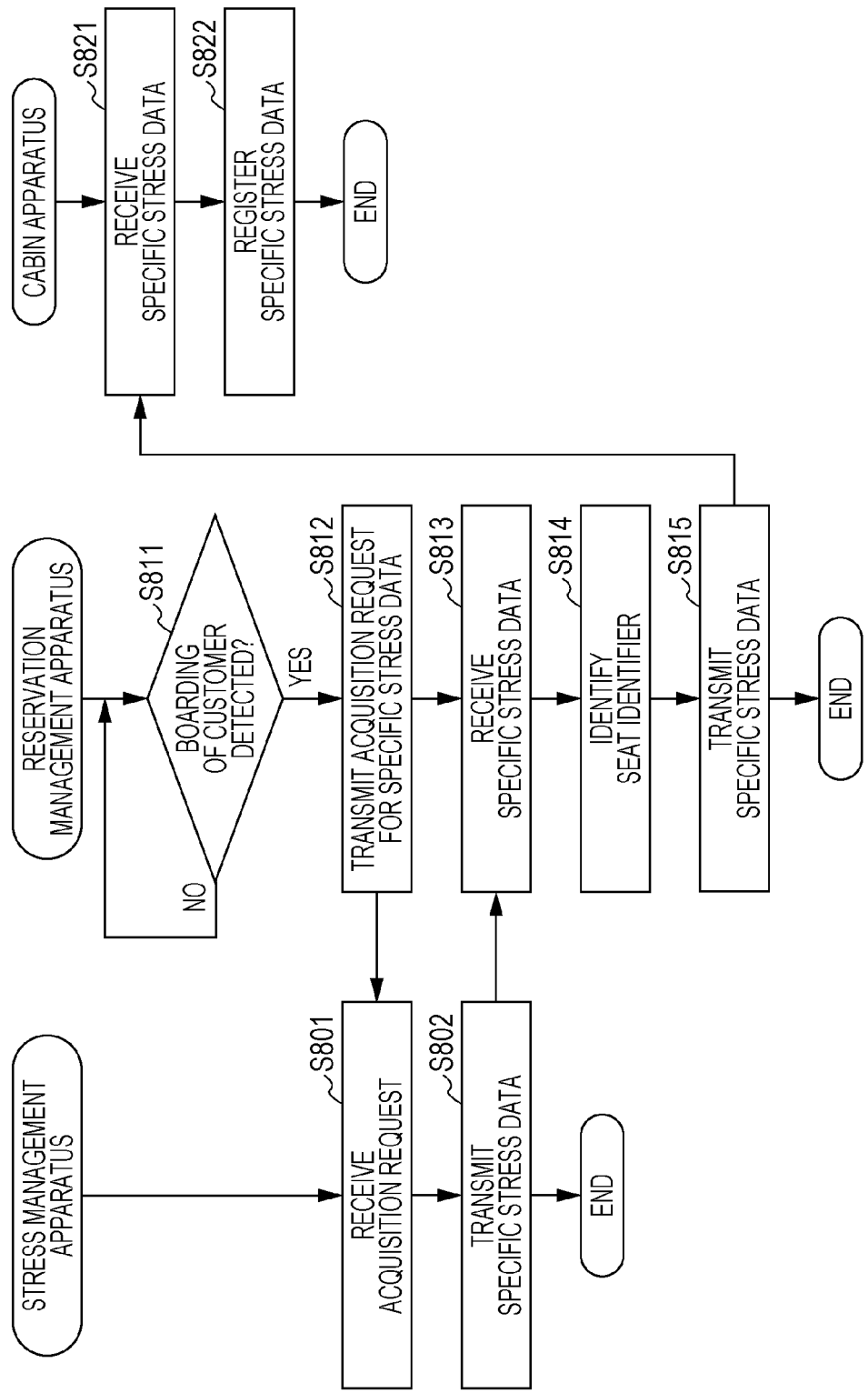
FIG. 10 is a flowchart that illustrates one example of a process at a time when a customer boards a boarding flight in the stress alleviation system according to the first embodiment of the present disclosure.

FIG. 10 is a flowchart that illustrates one example of a process at a time when the customer 102 boards the boarding flight in the stress alleviation system 1 according to the first embodiment of the present disclosure.

First, in a case where boarding of the customer 102 is detected (YES in S811), the processing unit 310 of the reservation management apparatus 30 transmits the acquisition request for the specific stress data that include the customer identifier of the detected customer 102 to the stress management apparatus 20 (S812). Here, the processing unit 310 may assess that the concerned customer 102 is boarded in a case where the customer 102 passes through a boarding gate installed in an airport, a scanner provided to the boarding gate reads the customer identifier and the boarding flight identifier that are described on a boarding ticket of the customer 102, and the read customer identifier is received by the communication unit 330, for example. Further, the processing unit 310 may cause the customer identifier read by the scanner to be included in the acquisition request.

Next, the communication unit 240 of the stress management apparatus 20 receives the acquisition request (S801). Next, the processing unit 210 of the stress management apparatus 20 reads out the specific stress data of the customer who is indicated by the customer identifier included in the transmitted acquisition request from the specific stress table T3 (FIG. 6) and transmits the specific stress data to the reservation management apparatus 30 by using the communication unit 240 (S802).

Next, the communication unit 330 of the reservation management apparatus 30 receives the specific stress data (S813). Next, the processing unit 310 of the reservation management apparatus 30 refers to the reservation information table T4 by using the customer identifier included in the specific stress data that are received by the communication unit 330 and the boarding flight identifier that is read by the scanner in S811 and thereby specifies the seat identifier of the concerned customer 102 (S814). Referring to FIG. 7, in a case where the customer identifier included in the specific stress data is "10251451" and the boarding flight identifier is "August 15, PAL254, Itami→Haneda", the seat identifier is "line 3 A" is specified.

Next, the processing unit 310 associates the seat identifier specified in S814 with the specific stress data received in S813 and transmits the specific stress data to the cabin apparatus 10 by using the communication unit 330 (S815).

Next, the communication unit 141 of the cabin apparatus 10 receives the specific stress data that are transmitted from the reservation management apparatus 30 (S821). Next, the control unit 144 of the cabin apparatus 10 registers the specific stress data received by the communication unit 141 in the specific stress table T1 (FIG. 3) (S822). The above process is performed for each of the customers 102 of the boarding flight, and the specific stress table T1 in which the specific stress data of each of the customers 102 of the boarding flight are registered is built in the cabin apparatus 10.

In such a manner, in the stress alleviation system 1 according to the first embodiment, the inclination amount of the seat 101 is adjusted by the reclining mechanism 120 provided to the seat 101 on which each of the stressed customers sits, and the stressed state of each of the stressed customers is thereby alleviated. Consequently, even in a case where a cause of the stress to each of the stressed customers is included in service by a flight attendant, the stress to each of the stressed customers may be alleviated.

Further, whether or not each of the customers 102 is the stressed customer is assessed in accordance with the specific stress indicator that is specific to each of the customers 102, which is calculated from the biological data measured by the biological sensor 110 in the past boarding, as a reference. Thus, whether or not each of the customers 102 is the stressed customer may be assessed by a determination reference that corresponds to each of the customers 102.

Second Embodiment

Figure 11:
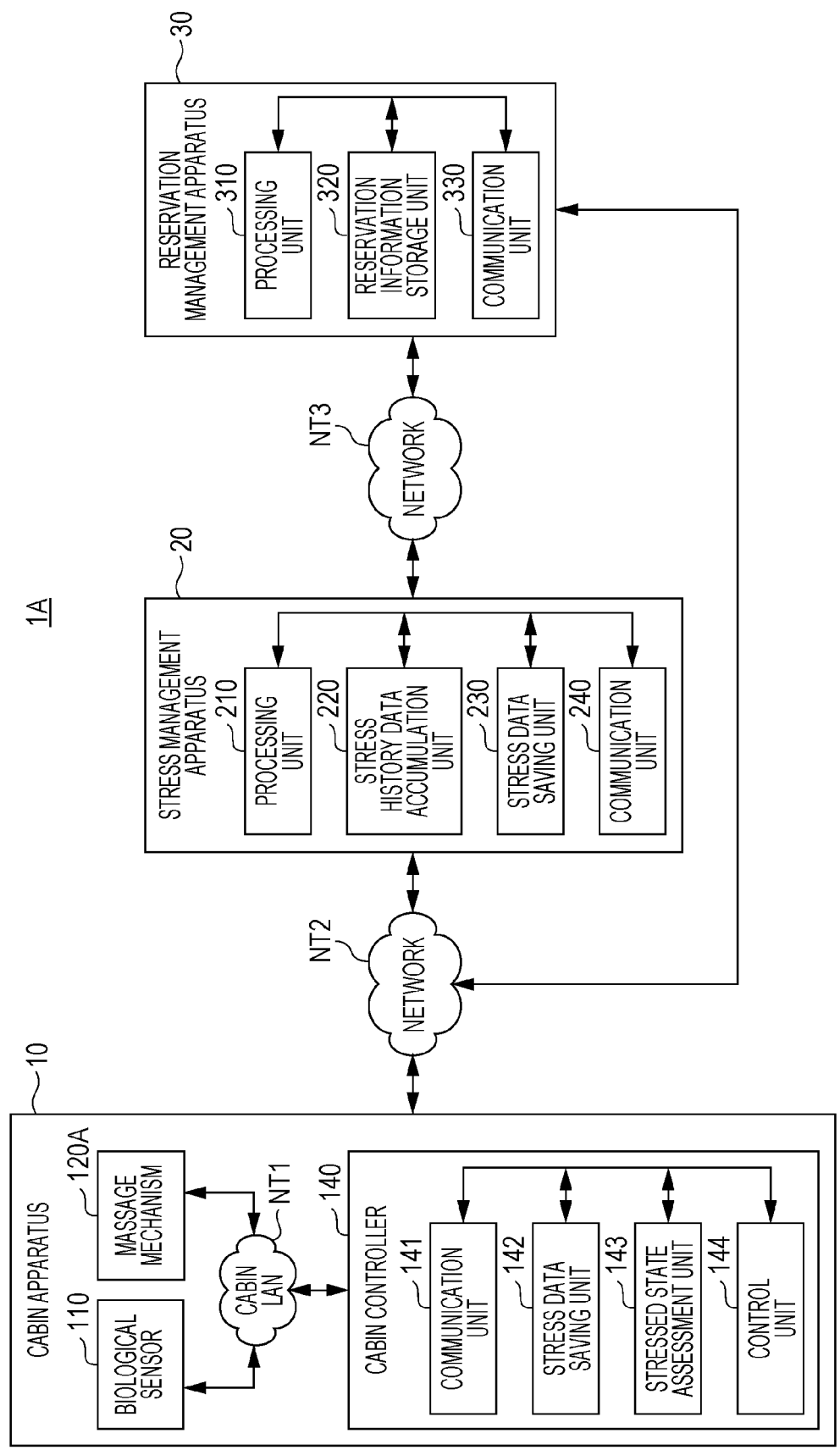
FIG. 11 is a diagram that illustrates one example of a general configuration of a stress alleviation system according to a second embodiment of the present disclosure.

FIG. 11 is a diagram that illustrates one example of a general configuration of a stress alleviation system 1A according to a second embodiment of the present disclosure. The stress alleviation system 1A has a characteristic that the reclining mechanism 120 in the stress alleviation system 1 is configured with a massage mechanism 120A. Note that in the second embodiment, the same reference characters will be given to the same configuration elements as the first embodiment, and a description will not be made.

The massage mechanism 120A is provided to each of one or more seats 101 and applies vibration to the customer 102 who sits on the seat 101 in accordance with a control signal that is transmitted from the cabin controller 140.

The massage mechanism 120A is configured with a vibrator provided to at least one of the back portion 101b and the seat portion 101a, for example, and the vibration with the strength in accordance with the control signal is applied to the customer 102 who sits on the seat 101.

Figure 12:
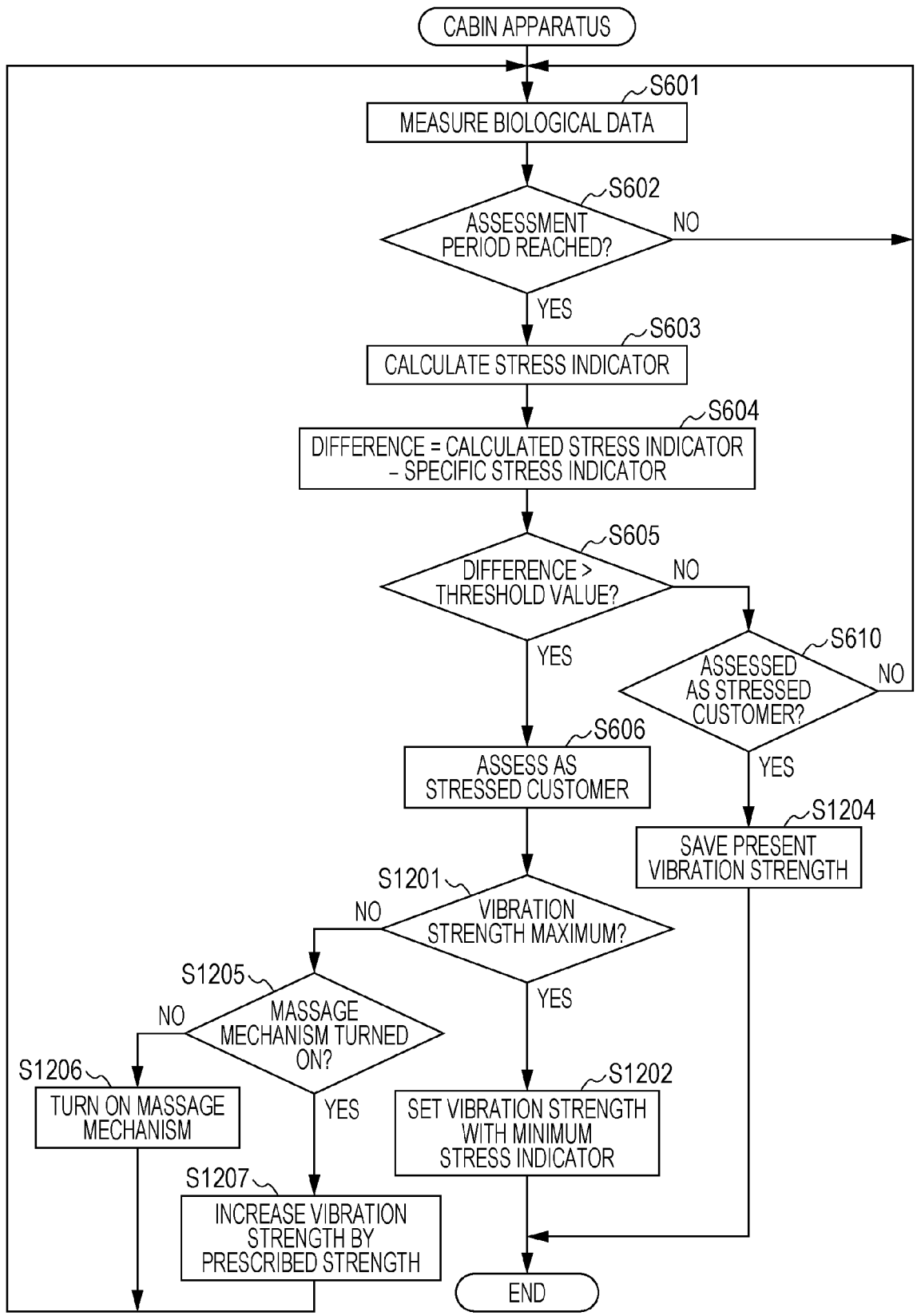
FIG. 12 is a flowchart that illustrates one example of a process of the cabin apparatus according to the second embodiment of the present disclosure.

FIG. 12 is a flowchart that illustrates one example of a process of the cabin apparatus 10 according to the second embodiment of the present disclosure. In FIG. 12, the same reference characters are provided to the processes that are the same as FIG. 8. Further, in this flowchart, it is assumed that the minimum vibration strength of the massage mechanism 120A is set as an initial vibration strength.

In S1201 that follows S606, in a case where the vibration strength of the massage mechanism 120A is not set to the maximum (NO in S1201), the process is caused to progress to S1205. In S1205, in a case where the massage mechanism 120A is not turned ON (NO in S1205), the control unit 144 transmits the control signal for turning ON the massage mechanism 120A to the massage mechanism 120A (S1206) and returns the process to S601. Accordingly, the massage mechanism 120A is turned ON, and vibration is applied to the stressed customer. In this case, the control signal for driving the massage mechanism 120A by the minimum vibration strength is transmitted.

On the other hand, in a case where the massage mechanism 120A is turned ON (YES in S1205), the control unit 144 transmits the control signal for increasing the vibration strength by predetermined strength to the massage mechanism 120A (S1207) and returns the process to S601.

On the other hand, in a case where the vibration strength of the massage mechanism 120A is the maximum (YES in S1201), the vibration strength may not be adjusted any more. Thus, the control unit 144 transmits the control signal for setting the vibration strength at which the stress indicator is the minimum to the massage mechanism 120A of the target customer (S1202) and finishes the process. Accordingly, even in a case where the vibration strength at which the difference in S604 is the threshold value or less may not be searched for in the range between the minimum vibration strength and the maximum vibration strength, setting is made to the vibration strength at which the stress indicator is the minimum, and the stress to the target customer may thereby be alleviated as much as possible.

In S1204 that follows YES in S610, the control unit 144 associates the present vibration strength with the customer identifier of the target customer and saves the present vibration strength as a learned vibration strength. Accordingly, the vibration strength that does not make the target customer in the stressed state may be learned. In this case, the control unit 144 transmits the learned vibration strength to the stress management apparatus 20 by using the communication unit 141 and may thereby save the learned vibration strength. This learned vibration strength may be employed as the initial vibration strength in the next time when the target customer boards the airplane X, for example. Note that in a case where the reservation management apparatus 30 makes the acquisition request for specific stress data, the stress management apparatus 20 may associate the learned vibration strength with the specific stress data as a transmission target and may thereby transmit the specific stress data to the reservation management apparatus 30.

In such a manner, in the stress alleviation system 1A according to the second embodiment, the massage mechanism 120A provided to the seat 101 of each of the stressed customers is turned ON, each of the stressed customers is thus relaxed, and the stress to each of the stressed customers may thereby be alleviated.

Third Embodiment

Figure 13:
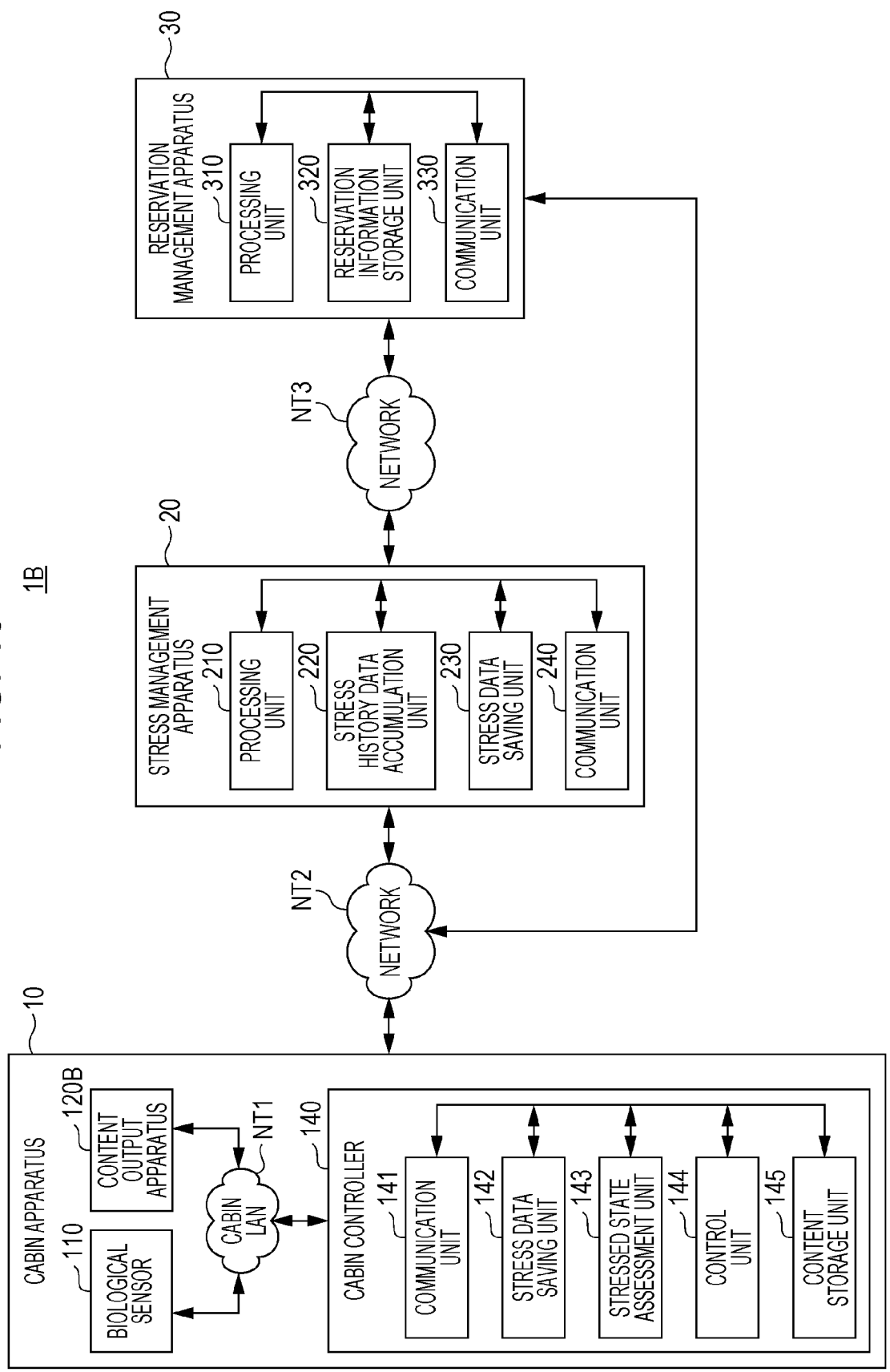
FIG. 13 is a diagram that illustrates one example of a general configuration of a stress alleviation system according to a third embodiment of the present disclosure.

FIG. 13 is a diagram that illustrates one example of a general configuration of a stress alleviation system 1B according to a third embodiment of the present disclosure. The stress alleviation system 1B has a characteristic that the reclining mechanism 120 in the stress alleviation system 1 is configured with a content output apparatus 120B. Note that in the third embodiment, the same reference characters will be given to the same configuration elements as the first embodiment, and a description will not be made.

The content output apparatus 120B are respectively provided to one or more seats 101. The content output apparatus 120B includes a video display apparatus and headphones and presents a content to the customer 102 who sits on the seat 101 in accordance with a control signal that is transmitted from the cabin controller 140. Here, as the contents, for example, music or videos that are created for the purpose of alleviating stress or combinations of music and videos may be employed. Alternatively, as the contents, for example, contents such as films and TV programs may be employed.

The cabin controller 140 includes a content storage unit 145 in addition to the configuration of FIG. 2. The content storage unit 145 is configured with a non-volatile storage apparatus and in advance stores one or more contents. The control unit 144 selects one content from the contents stored in the content storage unit 145 and delivers the one content to the content output apparatus 120E by using the communication unit 141. Here, the control unit 144 individually controls the content output apparatus 120B of each of the seats 101. Consequently, each of the content output apparatus 120E may individually output an appropriate content for the corresponding customer 102.

Figure 14:
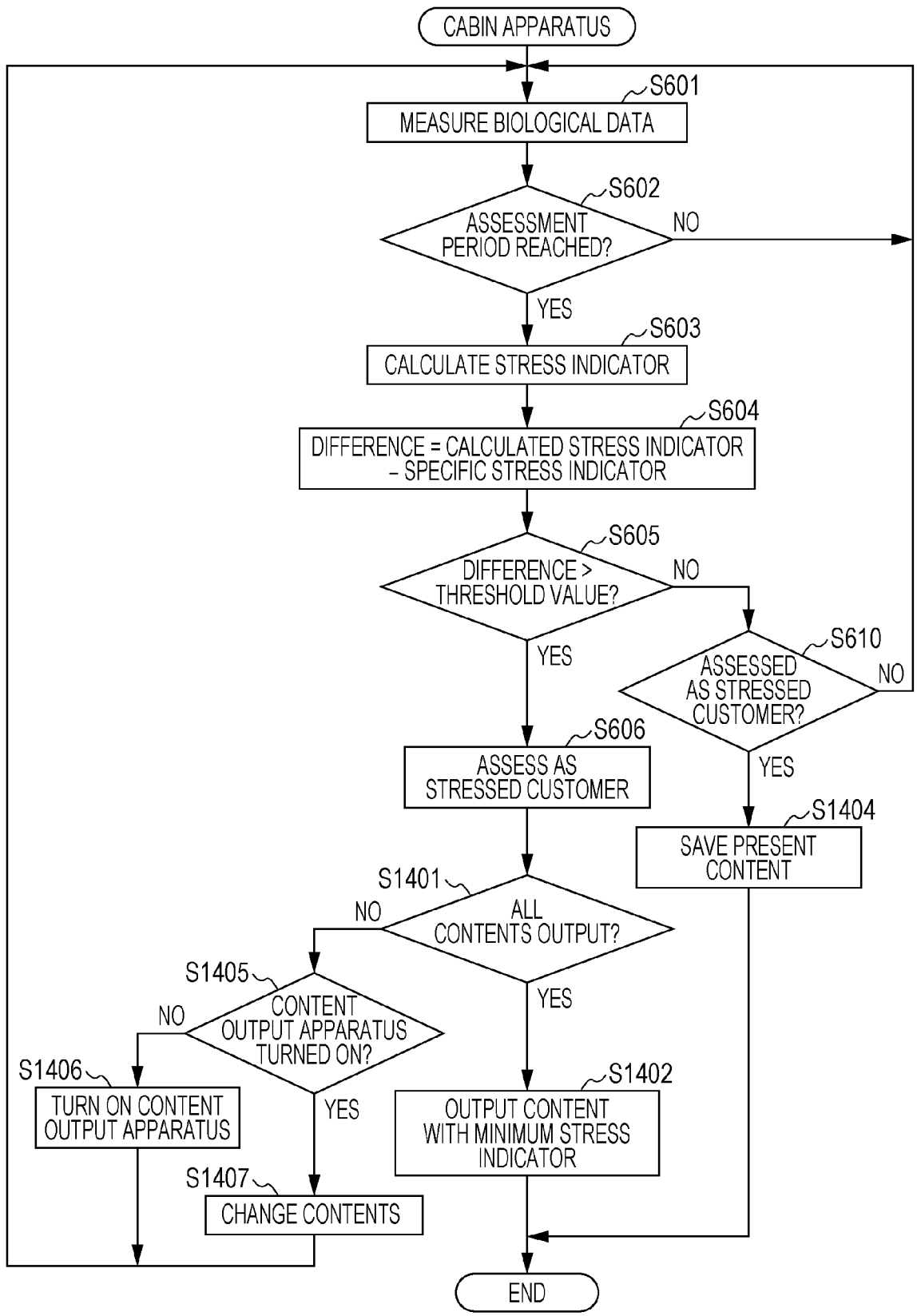
FIG. 14 is a flowchart that illustrates one example of a process of the cabin apparatus according to the third embodiment of the present disclosure.

FIG. 14 is a flowchart that illustrates one example of a process of the cabin apparatus 10 according to the third embodiment of the present disclosure. In FIG. 14, the same reference characters are provided to the processes that are the same as FIG. 8.

In S1401 that follows S606, in a case where all kinds of contents are not already output in the content output apparatus 120B (NO in S1401), the process is caused to progress to S1405. In S1405, in a case where the content output apparatus 120B is not turned ON (NO in S1405), the control unit 144 transmits the control signal for turning ON the content output apparatus 120B to the content output apparatus 120B (S1406) and returns the process to S601. Accordingly, the content output apparatus 120B is turned ON, and the content is presented to the stressed customer.

On the other hand, in a case where the content output apparatus 120B is turned ON (YES in S1405), the control unit 144 transmits the control signal for changing the contents to the content output apparatus 120E (S1407) and returns the process to S601.

On the other hand, in a case where the content output apparatus 120E outputs all kinds of contents (YES in S1401), the contents may not be changed any more. Thus, the control unit 144 transmits the control signal for outputting the content with which the stress indicator is the minimum to the content output apparatus 120E (S1402) and finishes the process. Accordingly, even in a case where the content with which the difference in S604 is the threshold value or less may not be presented, the content with which the stress indicator is the minimum is presented, and the stress to the target customer may thereby be alleviated as much as possible.

In S1404 that follows YES in S610, the control unit 144 associates the presently presented content with the customer identifier of the target customer and saves the presently presented content as a learned content. Accordingly, the content that does not make the target customer in the stressed state may be learned. In this case, the control unit 144 transmits an identifier of the learned content to the stress management apparatus 20 by using the communication unit 141 and may thereby save the identifier of the learned content. This identifier of the learned content may be employed as the initial content in the next time when the target customer boards the airplane X, for example. Note that in a case where the reservation management apparatus 30 makes the acquisition request for the specific stress data, the stress management apparatus 20 may associate the identifier of the learned content with the specific stress data as a transmission target and may thereby transmit the specific stress data to the reservation management apparatus 30.

In such a manner, in the stress alleviation system 1B according to the third embodiment, the content is presented to each of the stressed customers, each of the stressed customers is thus relaxed, and the stress to each of the stressed customers may thereby be alleviated.

Fourth Embodiment

A stress alleviation system 1C according to a fourth embodiment has a characteristic that a second customer who is more important than a first customer is more easily assessed as the stressed customer than the first customer. The second customers are classified as customers who sit on special seats on board (for example, first class and business class) and customers whose frequent flyer points are a certain value or more. The first customer is classified as the other customer than the second customer.

Note that in the fourth embodiment, the same reference characters will be given to the same configuration elements as the first to third embodiments, and a description will not be made. Further, the fourth embodiment is applicable to cases where the configurations of any of the first to third embodiments are employed. However, in the following description, a description will be made about an example where the configuration of the first embodiment is employed. Consequently, in the stress alleviation system 1C according to the fourth embodiment, the general configuration is the same as FIG. 1 and FIG. 2.

Referring to FIG. 2, in the fourth embodiment, the stressed state assessment unit 143 of the cabin apparatus 10 assesses the first customer as the stressed customer in a case where the difference that results from the subtraction of the specific stress indicator from the stress indicator calculated from the biological data is greater than a first threshold value TH1. Meanwhile, the stressed state assessment unit 143 assesses the second customer as the stressed customer in a case where the difference is greater than a second threshold value TH2 (<TH1). Accordingly, the stressed state of the second customer may be alleviated at an earlier stage than the first customer.

FIG. 15 is a diagram that illustrates one example of a data configuration of a customer table T5 that is used in the stress alleviation system 1C according to the fourth embodiment of the present disclosure. The customer table T5 is in advance stored in the reservation information storage unit 320 of the reservation management apparatus 30, for example. The customer table T5 is a database in which one piece of customer data is assigned to one record and includes fields of "customer identifier", "name", "frequent flyer points", and "attribute". "Customer identifier" is the same as FIG. 3. In the field of "name", the name of the customer is registered. In the field of "frequent flyer points", the frequent flyer points possessed by the customer are registered. The frequent flyer points are points whose value increases as the total distance in which the customer 102 boards airplanes of the concerned airline company increases, for example. In the field of "attribute", the data that indicate whether or not the customer has the attribute of the second customer are registered. Here, in a case where "premium" is registered in the field of "attribute", the customer is the second customer. Here, the attribute of "premium" is given to the customer whose frequent flyer points are a certain value or more or whose frequency of boarding with the special seats is a certain value or more. Note that the customer who sits on the special seat on board may be treated as the second customer. In this case, whether or not the customer sits on the special seat on board may be specified by the seat identifier.

Note that in a case where the processing unit 310 of the reservation management apparatus 30 transmits the specific stress data to the cabin apparatus 10, the processing unit 310 may refer to the customer table T5 and assess whether or not the concerned customer is the second customer. In a case where the concerned customer is the second customer, the processing unit 310 may associate the information that indicates this fact with the specific stress data and transmits the specific stress data to the cabin apparatus 10. Accordingly, the stressed state assessment unit 143 of the cabin apparatus 10 may determine whether or not which customer 102 is the second customer.

As described above, in the stress alleviation system 1C according to the fourth embodiment, because the second threshold value that is the threshold value for the second customer is set lower than the first threshold value for the first customer, the stress to the second customer may be alleviated early. Note that, as the second threshold value, a value may be employed at which the customer 102 may not be concluded to be in the stressed state but the possibility that the customer 102 is in the stressed state may not be denied.

The present disclosure may employ the following modifications.

(1) In S611 in FIG. 8, the process is finished after the present inclination amount is saved. However, the process may be returned to S601, and whether or not the target customer matches the stressed customer may again be monitored. Further, in S1204 in FIG. 12, the process is finished after the present vibration strength is saved. However, the process may be returned to S601, and whether or not the target customer matches the stressed customer may again be monitored. Further, in S1404 in FIG. 14, the process is finished after the presently presented content is saved. However, the process may be returned to S601, and whether or not the target customer matches the stressed customer may again be monitored.

(2) In the first to fourth embodiments, the stress management apparatus 20 and the reservation management apparatus 30 are configured with different computers. However, the present disclosure is not limited to this, but the stress management apparatus 20 and the reservation management apparatus 30 may be configured with one computer.

(3) In the second embodiment, the massage mechanism 120A applies vibration to the customer 102. However, the present disclosure is not limited to this, but a massaging motion may be applied. In this case, the massage mechanism 120A may be configured with a treatment element that performs the massaging motion for the customer 102.

(4) In the third embodiment, the content is automatically output for the stressed customer. However, the present disclosure is not limited to this, but a message by a voice or an image that recommends watching or listening to the content may be output.

(5) In the above embodiments, a description is made that the sensor which uses the millimeter-wave radar or the pressure sensing tube may be employed as the biological sensor 110. However, the present disclosure is not limited to this.

For example, Japanese Patent No. 5735592 discloses that the comfortableness of a user is evaluated by 10 levels of −5 to +5 from the biological data such as a heart rate, a pulse, and a body temperature. Accordingly, in the present disclosure, the comfortableness disclosed in Japanese Patent No. 5735592 may be employed as the stress indicator. In this case, the stress indicator may be calculated from a brain wave, a brain blood flow, a pulse wave, a blood pressure, a respiration rate, the body temperature, and a sweat rate.

Further, Japanese Unexamined Patent Application Publication No. 2012-249797 discloses that a value that results from a linear combination of the heart rate, the body temperature, the blood pressure, and the sweat rate is calculated as the stress value. Accordingly, in the present disclosure, the stress value disclosed in Japanese Unexamined Patent Application Publication No. 2012-249797 may be employed as the stress indicator.

Further, for example, Japanese Unexamined Patent Application Publication (Translation of PCT Application) No. 2003-534864 discloses a technique for assessing the stress to a person by using thermal image data of a face surface of the person. Accordingly, in the present disclosure, the stress indicator may be calculated by using the technique disclosed in Japanese Unexamined Patent Application Publication (Translation of POT Application) No. 2003-534864.

The present disclosure may alleviate stress to a customer who is boarded on an airplane and is thus useful for aviation systems for providing service for customers.

What is claimed is:

1. A stress alleviation system, comprising:
a biological sensor that measures first biological data of a customer on board a transportation vehicle for calculating a first stress indicator of the customer;
a seat of the transportation vehicle that includes circuitry for receiving a signal, and applies an action to the customer for alleviating a stressed state of the customer sitting on the seat;
a memory that in advance saves specific stress data in which a customer identifier and a second stress indicator are associated with each other, the customer identifier identifying the customer, the second stress indicator being calculated by using second biological data of the customer, the second biological data being measured while on board in the past;
a processor that
assesses whether or not the customer is in the stressed state by calculating the first stress indicator of the customer on board using the first biological data of the customer, and by comparing the first stress indicator and the second stress indicator; and
transmits a control signal to the seat including the circuitry in a case where the customer is assessed as in the stressed state, the control signal causing the seat to apply the action to the customer,
wherein the seat includes a reclining mechanism that inclines the seat,
wherein the processor transmits the control signal that causes the reclining mechanism to perform an adjustment in an inclination amount of the seat of the customer based on a difference between the second stress indicator and the first stress indicator,
wherein the processor assesses the customer as being in the stressed state in a case where the difference between the second stress indicator and the first stress indicator is greater than a predetermined threshold value,
wherein the processor
assesses the customer as in the stressed state in a case where the customer is a first customer and where a difference between the first stress indicator and the second stress indicator is greater than a first threshold value, and
assesses the customer as in the stressed state in a case where the customer is a second customer and where the difference is greater than the second threshold value that is greater than the first threshold value, and
wherein the second customer is less important than the first customer.

2. The stress alleviation system according to claim 1, wherein
the biological sensor is a non-contact type that measures the first biological data without contacting the customer.

3. The stress alleviation system according to claim 1, wherein
the seat includes a massage mechanism that massages the customer sitting on the seat, and
the processor transmits the control signal that causes the massage mechanism provided to the seat of the customer to turn on.

4. The stress alleviation system according to claim 1, wherein
the seat is connected to a display or a speaker that outputs a content for alleviating the stressed state of the customer sitting on the seat, and
the processor transmits the control signal that causes the display or the speaker corresponding to the seat of the customer to output the content.

5. The stress alleviation system according to claim 1, wherein the processor changes a type or strength of the action, in a case where the customer is assessed as in the stressed state.

6. The stress alleviation system according to claim 5, wherein the processor applies an action with which the first stress indicator becomes a minimum among actions applied to the customer, in a case where the stressed state of the customer is not removed even when the type or strength of the action is changed.

7. The stress alleviation system according to claim 1, wherein the adjustment in the inclination amount is less than a maximum adjustment available.

8. The stress alleviation system according to claim 1, wherein the adjustment in the inclination amount corresponding to the first stress indicator is less than an adjustment for relieving maximum amount of stress of the customer.

9. The stress alleviation system according to claim 1, wherein the memory further stores stress indicator information with respect to a specific seat identifier or location within the transportation vehicle, which contributes to the first stress indicator.

10. The stress alleviation system according to claim 1, wherein the memory further stores flight information, which contributes to the first stress indicator, and
wherein the flight information includes route information.

11. The stress alleviation system according to claim 1, wherein the biological sensor is disposed on a top surface of a back portion of the seat.

12. The stress alleviation system according to claim 1, wherein the transportation vehicle is a mass transportation vehicle.

13. The stress alleviation system according to claim 1, wherein the transportation vehicle is an air plane.

14. The stress alleviation system according to claim 1, wherein
the processor determines identity of the customer based on seat assignment information received prior to the customer occupying the seat of the transportation vehicle.

15. The stress alleviation system according to claim 1, wherein
the first biological data includes at least one of a brain wave, a brain blood flow, a pulse wave, a blood pressure, a respiration rate, a body temperature, or a sweat rate.

16. A stress alleviation method, comprising:
measuring, by a biological sensor, first biological data of a customer on board a transportation vehicle for calculating a first stress indicator of the customer;
acquiring specific stress data in which a customer identifier and a second stress indicator are associated with each other, the customer identifier identifying the customer, the second stress indicator being calculated by using second biological data measured while on board in the past;
assessing, by a processor, that the customer is in a stressed state by calculating the first stress indicator of the customer on board using the first biological data of the customer, and by comparing the first stress indicator and the second stress indicator; and
transmitting, by the processor, a control signal to a seat of the customer including circuitry in response to assessing that the customer is in the stressed state, the control signal causing the seat to apply an action to the customer,
wherein the seat includes a reclining mechanism that inclines the seat,
wherein the control signal that causes the reclining mechanism to adjust an inclination amount of the seat of the customer is based on a difference between the second stress indicator and the first stress indicator,
wherein, in the assessing, the difference between the second stress indicator and the first stress indicator being greater than a predetermined threshold value indicates that the customer is in the stressed state,
wherein a difference between the first stress indicator and the second stress indicator being greater than a first threshold value indicates that a first customer is in the stressed state,
wherein the difference being greater than the second threshold value indicates that a second customer is in the stressed state,
wherein the second threshold value is greater than the first threshold value, and
wherein the second customer is less important than the first customer.

17. A stress alleviation system, comprising:
a biological sensor that measures first biological data of a customer on board a transportation vehicle for calculating a first stress indicator of the customer;
a seat of the transportation vehicle that includes circuitry for receiving a signal, and applies an action to the customer for alleviating a stressed state of the customer sitting on the seat:
a memory that in advance saves specific stress data in which a customer identifier and a second stress indicator are associated with each other, the customer identifier identifying the customer, the second stress indicator being calculated by using second biological data of the customer, the second biological data being measured while on board in the past
a processor that
assesses whether or not the customer is in the stressed state by calculating the first stress indicator of the customer on board using the first biological data of the customer, and by comparing the first stress indicator and the second stress indicator; and
transmits a control signal to the seat including the circuitry in a case where the customer is assessed as in the stressed state, the control signal causing the seat to apply the action to the customer,
wherein the seat includes a reclining mechanism that inclines the seat,
wherein the processor transmits the control signal that causes the reclining mechanism to perform an adjustment in an inclination amount of the seat of the customer based on a difference between the second stress indicator and the first stress indicator,
wherein the processor assesses the customer as being in the stressed state in a case where the difference between the second stress indicator and the first stress indicator is greater than a predetermined threshold value,
wherein the processor
assesses the customer as in the stressed state in a case where the customer is a first customer and where a difference between the first stress indicator and the second stress indicator is greater than a first threshold value, and
assesses the customer as in the stressed state in a case where the customer is a second customer and where the difference is greater than the second threshold value that is greater than the first threshold value,
wherein the second customer is less important than the first customer, and
wherein the biological sensor measures the first biological data by radiating millimeter-wave towards the customer and without contacting the customer.

* * * * *